United States Patent
Cho et al.

(10) Patent No.: US 9,683,123 B2
(45) Date of Patent: Jun. 20, 2017

(54) SILVER INK

(71) Applicant: PESOLVE CO., LTD., Ansan (KR)

(72) Inventors: Hyun Nam Cho, Gunpo (KR); Hyun Ju Kim, Gunpo (KR)

(73) Assignee: PESOLVE CO., LTD., Ansan-si (KR)

( * ) Notice: Subject to any disclaimer, the term of this patent is extended or adjusted under 35 U.S.C. 154(b) by 0 days.

(21) Appl. No.: 14/787,031

(22) PCT Filed: Aug. 5, 2014

(86) PCT No.: PCT/KR2014/007248
§ 371 (c)(1),
(2) Date: Oct. 26, 2015

(87) PCT Pub. No.: WO2016/021748
PCT Pub. Date: Feb. 11, 2016

(65) Prior Publication Data
US 2016/0168408 A1    Jun. 16, 2016

(51) Int. Cl.
| | | |
|---|---|---|
| H01B 1/02 | (2006.01) | |
| H01B 1/20 | (2006.01) | |
| C09D 11/52 | (2014.01) | |
| C07C 55/02 | (2006.01) | |
| C07C 55/22 | (2006.01) | |
| C07C 55/24 | (2006.01) | |
| C07C 57/13 | (2006.01) | |
| C07C 57/18 | (2006.01) | |
| C07C 59/285 | (2006.01) | |
| C07C 59/347 | (2006.01) | |
| C07C 59/58 | (2006.01) | |
| C07C 251/08 | (2006.01) | |
| C07C 323/54 | (2006.01) | |
| C07C 251/72 | (2006.01) | |

(52) U.S. Cl.
CPC .............. *C09D 11/52* (2013.01); *C07C 55/02* (2013.01); *C07C 55/22* (2013.01); *C07C 55/24* (2013.01); *C07C 57/13* (2013.01); *C07C 57/18* (2013.01); *C07C 59/285* (2013.01); *C07C 59/347* (2013.01); *C07C 59/58* (2013.01); *C07C 251/08* (2013.01); *C07C 251/72* (2013.01); *C07C 323/54* (2013.01); *H01B 1/02* (2013.01)

(58) Field of Classification Search
CPC ... H01B 1/02; H01B 1/22; H01B 1/20; C09D 11/52
See application file for complete search history.

(56) References Cited

U.S. PATENT DOCUMENTS

| | | |
|---|---|---|
| 7,691,294 B2 | 4/2010 | Chung et al. |
| 8,226,755 B2 | 7/2012 | Chung et al. |
| 2008/0003364 A1 | 1/2008 | Ginley et al. |
| 2010/0009153 A1 | 1/2010 | Yang et al. |
| 2010/0084599 A1 | 4/2010 | Lewis et al. |
| 2010/0193751 A1* | 8/2010 | Heo .................. H01B 1/22 252/514 |
| 2011/0008548 A1 | 1/2011 | Smith et al. |
| 2011/0111138 A1 | 5/2011 | McCullough et al. |
| 2011/0183128 A1 | 7/2011 | Magdassi et al. |

FOREIGN PATENT DOCUMENTS

| | | |
|---|---|---|
| JP | 2014-080579 A | 5/2014 |
| JP | 2014-082184 A | 5/2014 |
| JP | 2014-080581 A | 8/2014 |
| KR | 10-2007-0081546 A | 5/2013 |
| WO | 2007/004437 A1 | 1/2007 |
| WO | 2009/059273 A2 | 5/2009 |
| WO | 2010/011974 A1 | 1/2010 |
| WO | 2012/114925 A1 | 8/2012 |

OTHER PUBLICATIONS

Synthesis of Silver Nanoparticles from the Decomposition of Silver(I) [bis(alkylthio)methylene]malonate Complexes, Euyjin Lee et al., Bull. Korean Chem. Soc. 2012, vol. 33, No. 1, 60-64.*
Binnemans, et al., "Structure and Mesomorphism of Silver Alkanoates", Chem. Mater. 2004, 16, pp. 2021-2027.
Chi, et al., "Synthesis and Characterization of (B-Diketonato) silver Vinyltriethylsilane Compounds and Their Application to CVD of Silver Thin Films. Crystal Structure of the (2,2-Dimethyl-6,6,7,7,8,8,8-heptafluoro-3,5-octanedionato)silver Vinyltriethylsilane Dimer", American Chemical Society, Organometallics 1996, 15, pp. 2575-2578.
Chun, et al., "Roll-to-Roll Printing of Silver Oxide Pastes and Low Temperature Conversion to Silver Patterns", Chem. Mater. 2009, 21, pp. 343-350.
Dearden, et al., "A Low Curing Temperature Silver Ink for Use in Ink-Jet Printing and Subsequent Production of Conductive Tracks", Macromol. Rapid Commun. 2005, 26, pp. 315-318.
Fang, "Augmented instrumented indentation using nonlinear electrical contact current-voltage curves", J. Mater. Res., vol. 24, No. 5, May 2009, pp. 1820-1832.
Grouchko, et al., "Formation of air-stable copper-silver core-shell nanoparticles for inkjet printing", J. Mater. Chem., 2009, 19, pp. 3057-3062.
Lee, "A Novel Solution-Stamping Process for Preparation of a Highly Conductive Aluminum Thin Film", Adv. Mater. 2011, 23, pp. 5524-5528.
Lee, et al., "Direct synthesis and inkjetting of silver nanocrystals toward printed electronics", Institute of Physics Publishing, Nanotechnology 17 (2002) pp. 2424-2428.
Rozenberg, et al., "Synthesis and Spectroscopic Studies of Novel B-Diketonate Copper(I) Compounds and Solid State Structure of Tetravinylsilane Tetrakis Copper (I) 1,1,1,5,5,5-Hexafluoroacetylacetonate (TVST[Cu]hfac)", American Chemical Society, Organometallics 2001, 20, pp. 4001-4005.
Smith, et al., "Direct ink-jet printing and low temperature conversion of conductive silver patterns", J. Mater Sci 41 (2006) pp. 4153-4158.
Szlyk, et al., "CVD of AGI Complexes with Tertiary Phosphines and Perfluorinated Carboxylates—A New Class of Silver Precursors", Chem. Vap. Deposition 2001, 7, No. 3, pp. 111-116.

(Continued)

*Primary Examiner* — Khanh Tuan Nguyen
*Assistant Examiner* — Haidung Nguyen
(74) *Attorney, Agent, or Firm* — STIP Law Group, LLC

(57) ABSTRACT

Provided is a silver ink including, as a major component, a silver malonate precursor represented by Formula 1 or Formula 2.

13 Claims, 8 Drawing Sheets

(56) References Cited

OTHER PUBLICATIONS

Walker, et al., "Reactive Silver Inks for Patterning High-Conductivity Features at Mild Temperatures", J. Am. Chem. Soc. 2012, 134, pp. 1419-1421.

Whitcomb, et al., "The molecular structure of [bis-triphenylphosphine-silver(I) stearate], [((C6H5)3P)2Ag(O2C(CH2)16CH3)], solubilization of long alkyl chain silver carboxylates", Journal of Chemical Crystallography, vol. 26, No. 2, 1996. pp. 99-105.

Wu, et al., "Synthesis of high-concentration Cu nanoparticles in aqueous CTAB solutions", Journal of Colloid and Interface Science 273 (2004) pp. 165-169.

\* cited by examiner

SILVER INK

CROSS-REFERENCE TO RELATED APPLICATIONS

This application is the U.S. National Phase under 35 U.S.C. §371 of International Application No. PCT/KR2014/007248 filed on Aug. 5, 2014, the disclosures of which are incorporated by reference into the present application.

TECHNICAL FIELD

The present invention relates to a silver ink, and more specifically to a silver ink including a silver precursor compound as a major component that has a high silver content, is highly stable, and can be calcined at low temperature, thus being directly applicable to various fields, including printed electronics.

BACKGROUND ART

In this century, the printed electronics industry has developed as a nanotechnology-based environmentally friendly convergence industry and has been considered a new paradigm to overcome the limitations of existing industries. In the printed electronics industry, new concepts of electronic materials and components are produced based on printing processes for mass production at low temperature and ambient pressure, achieving low cost, flexibility, and large area of products.

Under such circumstances, it is anticipated that a new market for electronic products will be created in the future in response to emotions, consumption patterns, and diverse needs of consumers and its size will surpass that of the existing markets. Numerous printed electronic products have been developed, for example, RFIDs, memories, a variety of displays (for example, OLEDs, ELs, electronic papers, and flexible displays), lighting devices, batteries (for example, secondary batteries and solar cells), touch panels, sensors, organic transistors, printed circuit boards (for example, PCBs and FPCBs), films for electromagnetic interference (EMI) shielding and transparent electrodes, and other applied products in various fields. These printed electronic products have opened up new markets. With the emergence of price competitive printed electronic products whose devices are freely designable, their market is expected to expand. Conventional processes for device production are partially limited by the kind and size of substrates employed, but printing processes are applicable irrespective of the kind, shape, and size of substrates. Particularly, printing processes are easily applied to large-size or flexible substrates and are recognized to be innovative in mass production of single products as well as small quantity batch production.

Suitable inks are essential for the manufacture of printed electronic products. Particularly, conductive inks are considered the most important materials for a variety of electrodes (including transparent electrodes). Specifically, an electronic ink composed of conductive metal nanoparticles or a metal precursor is directly printed (or coated) with an inkjet printer or a suitable printing system, such as a gravure printing, flexo printing, (rotary) screen printing, offset printing, gravure-offset printing or (nano)imprinting system, followed by drying or sintering to form a metal wire with a desired shape. This is essential for printed electronics processes.

Conductive inks necessary for printed electronics processes have been investigated and developed by many researchers. Generally, nanoparticle-based inks suffer from poor long-term storage stability or undergo aggregation of particles or precipitation, causing nozzle clogging during printing. For the purpose of preventing such problems, polymeric materials are usually used as stabilizers. However, excessive use of the stabilizers increases the viscosity of the inks or causes other problems, such as increased surface tension, high sintering temperature, and increased conductivity.

Conductive inks using metal nanoparticles can be found in Nanotechnology, 17, p 2424 (2006), J. Mater. Res., 24, p 1828 (2009), J. Colloid Interface. Sci., 273, p 165 (2004), J. Mater. Chem., 19, p 3057 (2009), US 2010/0084599 A1, US 2010/0009153A1, and US 2011/0183128A1.

The most commonly used approach to solve the problems of metal inks in the form of nanoparticles is to use organometallic salts or complexes as metal precursors. However, silver-containing carboxylic acid salts are generally sensitive to light, are not readily soluble, and have a high decomposition temperature, which limit their applicability despite ease of production. Attempts to solve such problems have been made, for example, by the use of silver precursors in which an electron donor, such as an amine or phosphine compound, is coordinated to a fluorinated carboxylic acid or a silver carboxylate having a long alkyl chain (Chem. Vapor Deposition, 7, pill (2001), Organometallics, 15, p 2575 (1996), Chem. Mater., 16, p 2021 (2004), and J. Chem. Crystallography, 26, p 99 (1996)). Such inks are described in the literature: for example, inks using such an organometallic complex or metal salt (U.S. Pat. No. 7,691,294 B2, US 2011/0111138A1, U.S. Pat. No. 8,226,755 B2, and J. Am. Chem. Soc., 134, 1419, 2012), an ink containing silver β-ketocarboxylate (WO 2007/004437A1), and inks using a silver neoalkanoate (Makromol Rapid Commun, 26, p 315 (2005), J. Mater. Sci., 41, p 4153 (2006), Chem. Mater., 21, p 343 (2009) and US 2011/0008548A1). In addition to the silver precursor inks, copper or aluminum precursor inks using inexpensive ink materials are also currently being developed (Organometallics, 20, p 4001 (2001), US 2008/0003364A1, Adv. Mater., 23, 5524, 2011, WO 2009/059273A2, and WO 2010/011974A1).

However, such metal complex inks have low metal solid contents or suffer from poor storage stability, which limit their application to products where highly reliable and conductive metal wires are needed.

The present inventors have made continued efforts to solve the problems of the prior art and finally arrived at the present invention.

DETAILED DESCRIPTION OF THE INVENTION

Problems to be Solved by the Invention

An object of the present invention is to provide a silver ink that is easy to produce, has a high silver content, is highly soluble and stable, and can be sintered at low temperature.

Means for Solving the Problems

According to one aspect of the present invention, there is provided a silver ink including, as a major component, a silver malonate precursor represented by Formula 1 or Formula 2:

[Formula 1]

$$\text{AgO} \underset{O}{\overset{R_1 \ R_2}{\diagdown}} \underset{O}{\diagup} \text{OAg} \quad (1)$$

wherein $R_1$ and $R_2$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, substituted or unsubstituted $C_5$-$C_{30}$ heteroaralkyl, —$(CH_2)_jOR^a$, —$(CH_2)_jC(O)R^a$, —$(CH_2)_jC(O)OR^a$, —$(CH_2)_jOC(O)R^a$, —$CH(C(O)OAg)_2$, —$(CH_2)_jOAg$, —$(CH_2)_jC(O)Ag$, —$(CH_2)_jC(O)OAg$, —$(CH_2)_jOC(O)Ag$, —$(CH_2)_jNR^bR^c$, —$(CH_2)_jC(O)NR^bR^c$, —$(CH_2)_jOC(O)NR^bR^c$, —$(CH_2)_jNR^dC(O)R^b$, —$(CH_2)_jNR^dC(O)OR^b$, —$(CH_2)_jNR^dC(O)NR^bR^c$, —$(CH_2)_jS(O)_mR^e$ or —$(CH_2)_jNR^dS(O)_mAg$ (where j is an integer from 0 to 12, m is an integer from 0 to 2, and $R^a$, $R^b$, $R^c$, $R^d$, and $R^e$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, or substituted or unsubstituted $C_5$-$C_{30}$ heteroaralkyl):

[Formula 2]

$$\text{AgO} \underset{O}{\overset{X}{\diagdown}} \underset{O}{\diagup} \text{OAg} \quad (2)$$

wherein X is oxygen (O), sulfur (S), $CR_1R_2$, $C(C(O)OAg)_2$, $C(SR_1)_2$, $C(SAg)_2$, $NR_1$ or $NNR_1R_2$ (where $R_1$ and $R_2$ are as defined in the above).

According to another aspect of the present invention, there is provided a conductive thin film formed by deposition of the silver ink.

Effects of the Invention

The silver ink of the present invention is easy to produce, has a high silver content, is highly soluble and stable, and can be sintered at low temperature.

MODE FOR CARRYING OUT THE INVENTION

Figure 1:
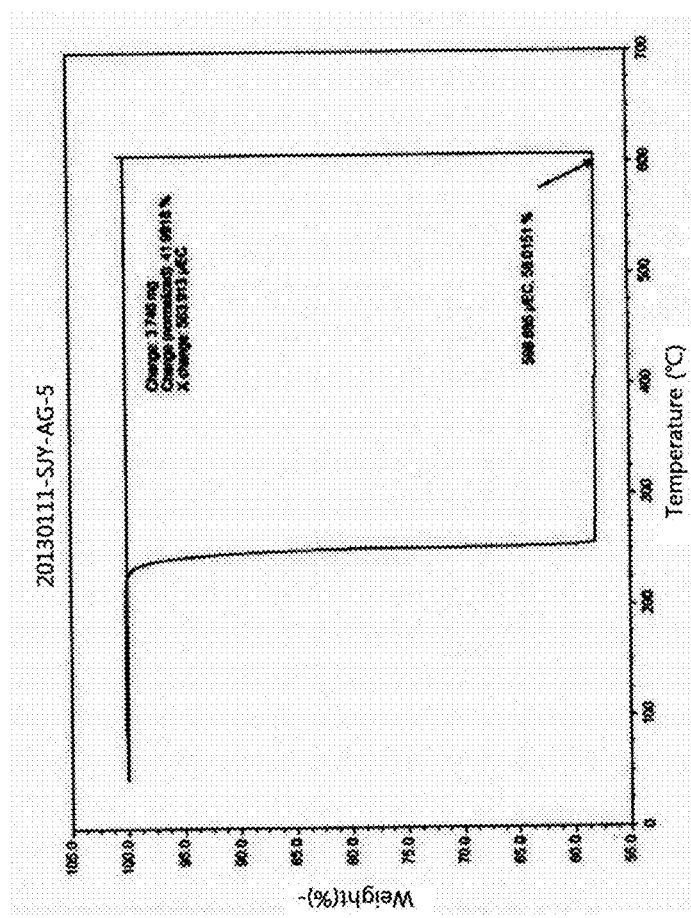
FIG. 1 shows thermogravimetric analysis (TGA) curves of a sample prepared in Example 1.
Figure 2:
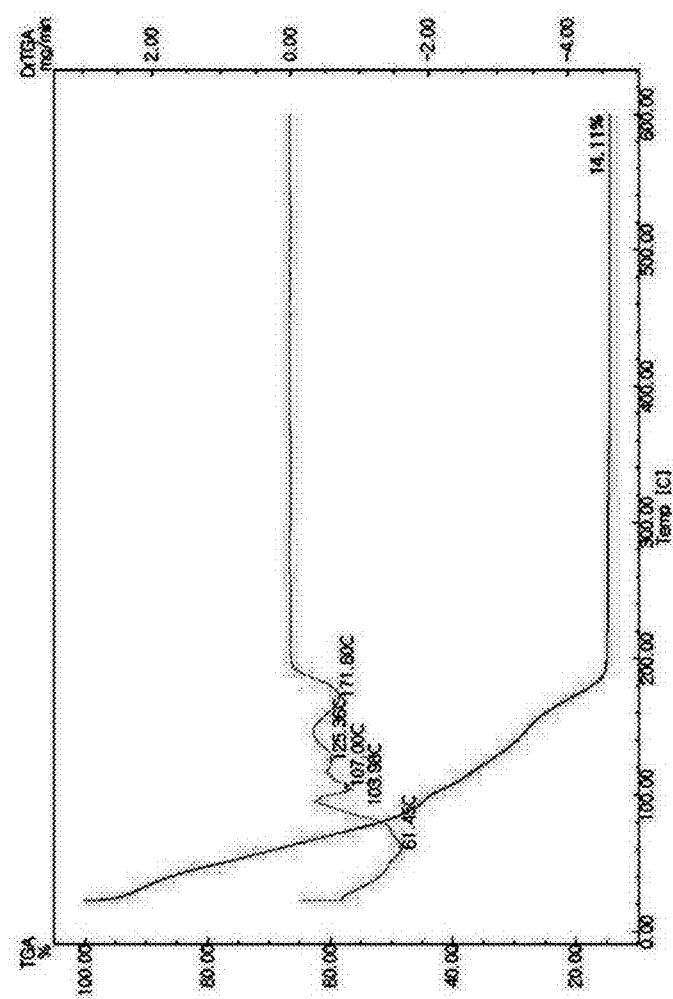
FIG. 2 shows TGA curves of a silver ink produced in Example 15.
Figure 3:
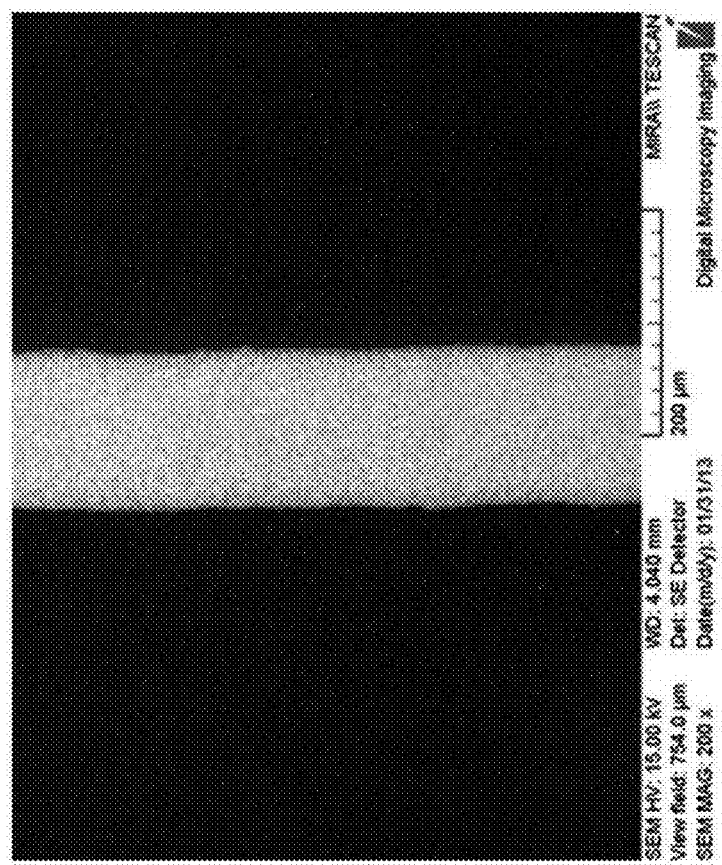
FIG. 3 is a surface electron microscopy (SEM) image of a paper sheet on which a silver ink produced in Example 15 was printed with an inkjet printer.
Figure 4:
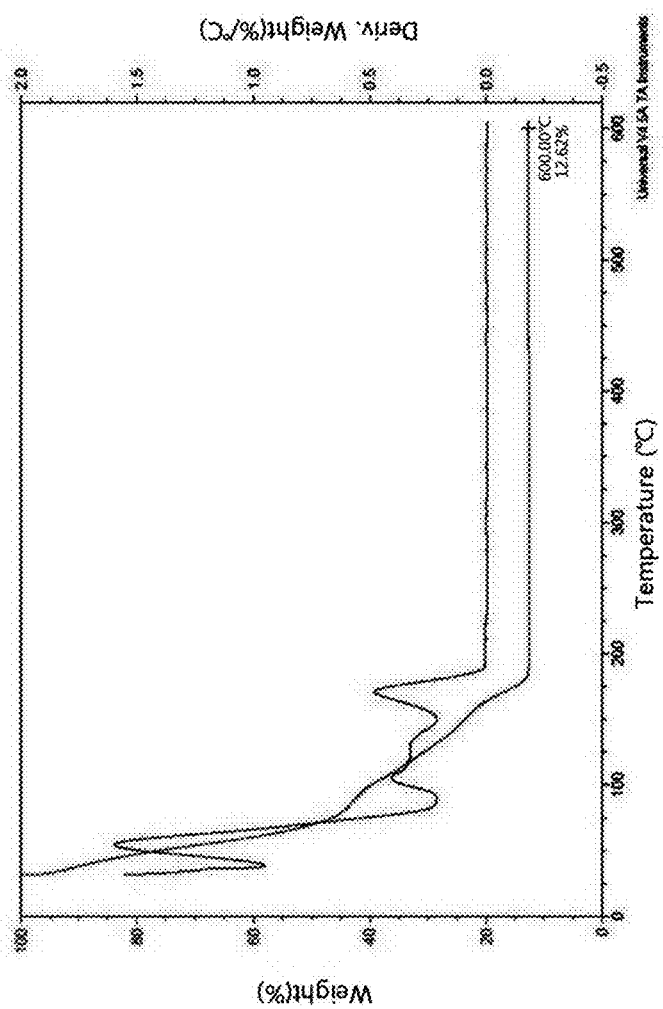
FIG. 4 shows TGA curves of a silver ink produced in Example 16.
Figure 5:
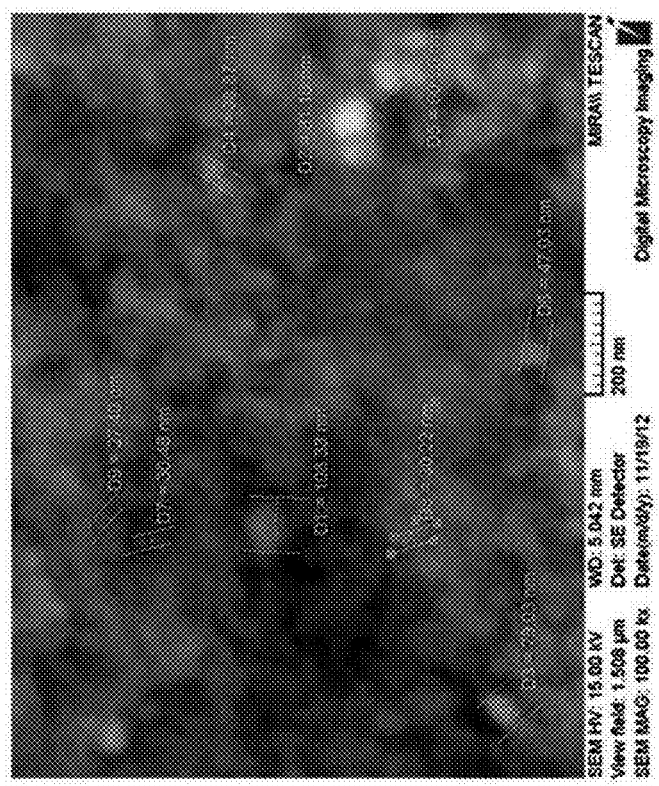
FIG. 5 is a surface electron microscopy (SEM) image of a mirror-like silver film formed in Example 16.
Figure 6:
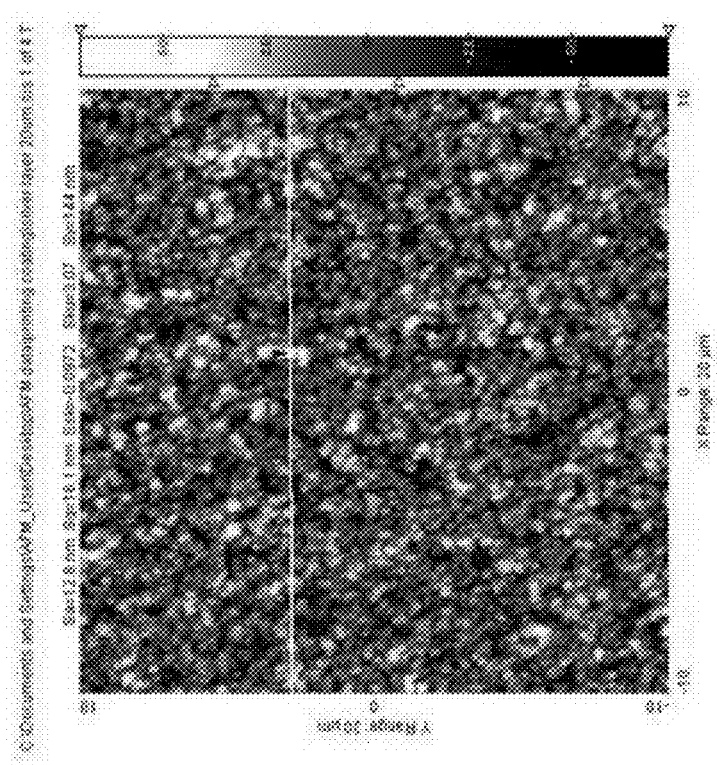
FIG. 6 is a surface atomic force microscopy (AFM) image of a mirror-like silver film formed in Example 16.
Figure 7:
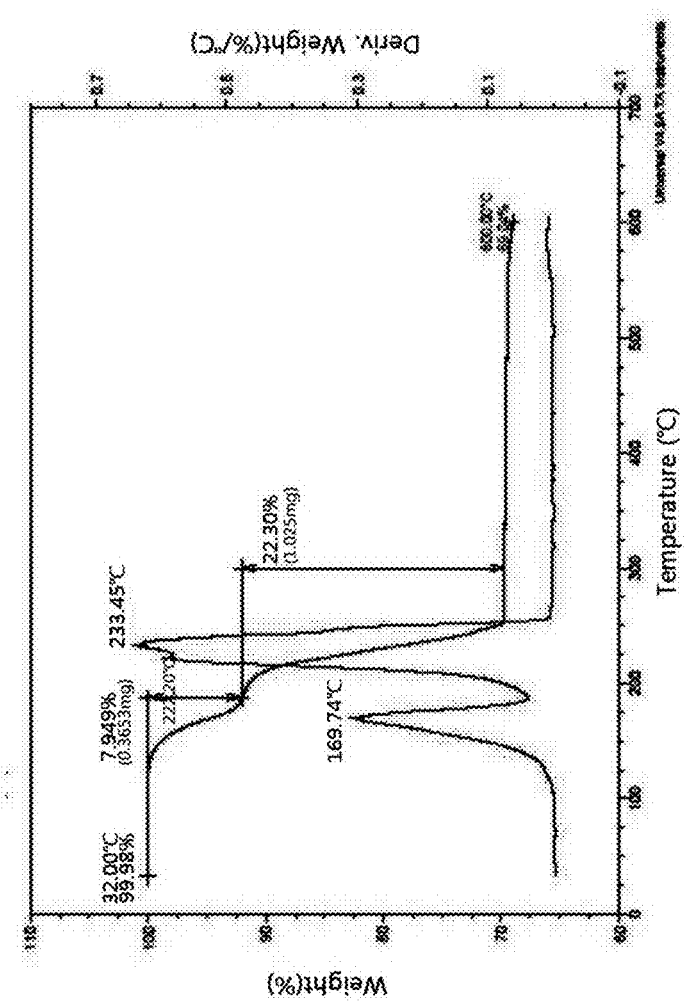
FIG. 7 shows TGA curves of a sample prepared in Example 7.
Figure 8:
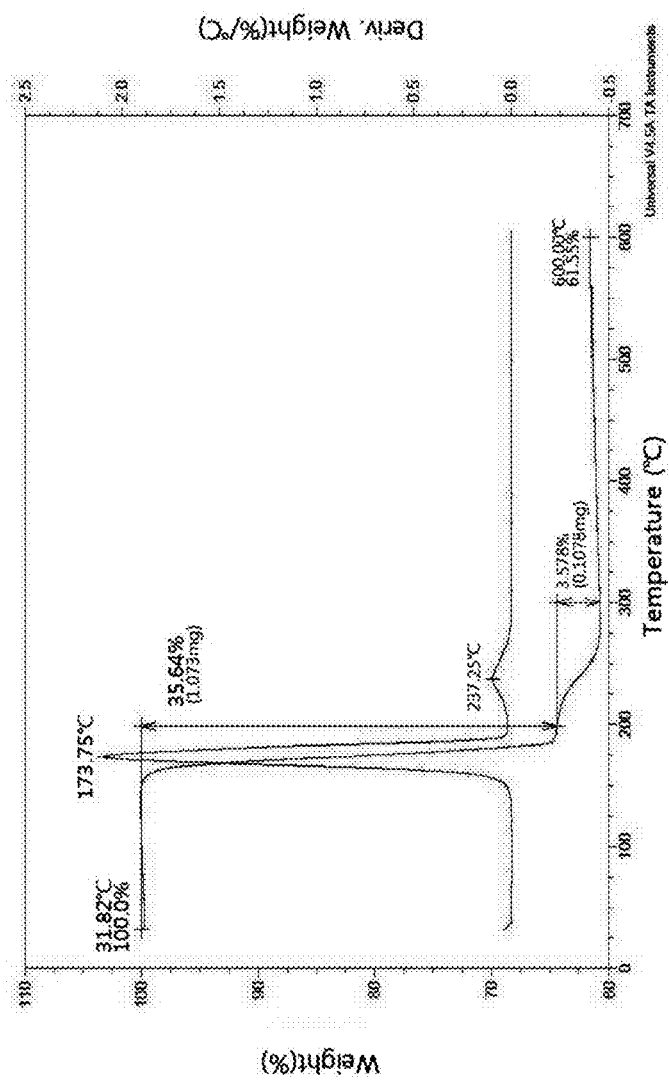
FIG. 8 shows TGA curves of a sample prepared in Example 13.

The term "alkyl" used herein includes straight, branched, cyclic hydrocarbon radicals, and combinations thereof. The term may optionally include one or more double bonds, triple bonds or a combination thereof in the chain. That is, "alkyl" is intended to include alkenes and alkynes.

The term "heteroalkyl", by itself or in combination with another term, means, unless otherwise stated, a stable straight, branched, cyclic hydrocarbon radical or a combination thereof, consisting of one or more carbon atoms and one or more heteroatoms selected from the group consisting of O, N, P, Si, and S, and wherein the nitrogen, phosphorus, and sulfur atoms may optionally be oxidized and the nitrogen heteroatom may optionally be quaternized.

The terms "cycloalkyl" and "heterocycloalkyl", by themselves or in combination with other terms, represent, unless otherwise stated, cyclic versions of "alkyl" and "heteroalkyl", respectively.

The term "aryl" means, unless otherwise stated, a polyunsaturated, aromatic, hydrocarbon substituent which can be a single ring or multiple rings (from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. The heteroaryl group can be attached to the remainder of the molecule through a carbon or heteroatom.

The term "aralkyl" refers to an alkyl group substituted with an aryl wherein the alkyl and aryl moieties independently are optionally substituted.

The term "heteroaralkyl" refers to an alkyl group substituted with a heteroaryl wherein the alkyl and heteroaryl moieties independently are optionally substituted.

The term "substituted" in the expression of "substituted or unsubstituted" described herein means that one or more hydrogen atoms in the hydrocarbon are each independently replaced by the same or different substituents.

Suitable substituents may include, but are not limited to one or more selected from the group consisting of —F; —Cl; —Br; —CN; —NO$_2$; —OH; $C_1$-$C_{20}$ alkyl groups substituted or unsubstituted with —F, —Cl, —Br, —CN, —NO$_2$ or —OH; $C_1$-$C_{20}$ alkoxy groups substituted or unsubstituted with —F, —Cl, —Br, —CN, —NO$_2$ or —OH; $C_6$-$C_{30}$ aryl groups substituted or unsubstituted with $C_1$-$C_{20}$ alkyl, $C_1$-$C_{20}$ alkoxy, —F, —Cl, —Br, —CN, —NO$_2$ or —OH; $C_6$-$C_{30}$ heteroaryl groups substituted or unsubstituted with $C_1$-$C_{20}$ alkyl, $C_1$-$C_{20}$ alkoxy, —F, —Cl, —Br, —CN, —NO$_2$ or —OH; $C_5$-$C_{20}$ cycloalkyl groups substituted or unsubstituted with $C_1$-$C_{20}$ alkyl, $C_1$-$C_{20}$ alkoxy, —F, —Cl, —Br, —CN, —NO$_2$ or —OH; $C_5$-$C_{30}$ heterocycloalkyl groups substituted or unsubstituted with $C_1$-$C_{20}$ alkyl, $C_1$-$C_{20}$ alkoxy, —F, —Cl, —Br, —CN, —NO$_2$ or —OH; and groups represented by —N(G$_1$)(G$_2$) (where G$_1$ and G$_2$ may be each independently hydrogen; a $C_1$-$C_{10}$ alkyl group; or a $C_6$-$C_{30}$ aryl group substituted or unsubstituted with $C_1$-$C_{10}$ alkyl).

The present invention provides a silver ink using, as a major component, a silver compound containing a specific malonate moiety. The silver ink of the present invention is characterized in that it has a high silver content, is highly soluble and stable, and can be calcined at low temperature.

The silver ink of the present invention includes, as a major component, a silver malonate precursor represented by Formula 1 or Formula 2:

[Formula 1]

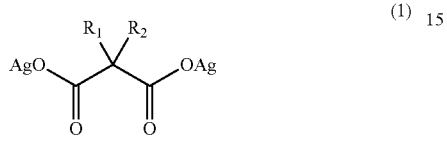
(1)

wherein $R_1$ and $R_2$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, substituted or unsubstituted $C_5$-$C_{30}$ heteroaralkyl, $-(CH_2)_jOR^a$, $-(CH_2)_jC(O)R^a$, $-(CH_2)_jC(O)OR^a$, $-(CH_2)_jOC(O)R^a$, $-CH(C(O)OAg)_2$, $-(CH_2)_jOAg$, $-(CH_2)_jC(O)Ag$, $-(CH_2)_jC(O)OAg$, $-(CH_2)_jOC(O)Ag$, $-(CH_2)_jNR^bR^c$, $-(CH_2)_jC(O)NR^bR^c$, $-(CH_2)_jOC(O)NR^bR^c$, $-(CH_2)_jNR^dC(O)R^b$, $-(CH_2)_jNR^dC(O)OR^b$, $-(CH_2)_jNR^dC(O)NR^bR^c$, $-(CH_2)_jS(O)_mR^e$ or $-(CH_2)_jNR^dS(O)_mAg$ (where j is an integer from 0 to 12, m is an integer from 0 to 2, and $R^a$, $R^b$, $R^c$, $R^d$, and $R^e$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, or substituted or unsubstituted $C_5$-$C_{30}$ heteroaralkyl):

[Formula 2]

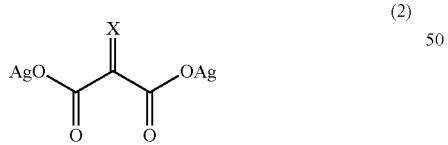
(2)

wherein X is oxygen (O), sulfur (S), $CR_1R_2$, $C(C(O)OAg)_2$, $C(SR_1)_2$, $C(SAg)_2$, $NR_1$ or $NNR_1R_2$ (where $R_1$ and $R_2$ are as defined in the above).

More specifically, $R_1$ and $R_2$ may be each independently selected from the group consisting of hydrogen, methyl, ethyl, n-propyl, iso-propyl, n-butyl, iso-butyl, t-butyl, n-pentyl, amyl, n-hexyl, 2-ethylhexyl, n-heptyl, octyl, iso-octyl, nonyl, decyl, dodecyl, hexadecyl, octadecyl, docodecyl, cyclopropyl, cyclopentyl, cyclohexyl, allyl, propargyl, acetyl, benzoyl, hydroxyethyl, methoxyethyl, 2-hydroxypropyl, methoxypropyl, aminoethyl, cyanoethyl, mercaptoethyl, chloroethyl, methoxy, ethoxy, butoxy, hexyloxy, phenoxy, methoxyethoxyethyl, methoxyethoxyethoxyethyl, imidazolyl, carboxymethyl, trimethoxysilylpropyl, triethoxysilylpropyl, phenyl, methoxyphenyl, cyanophenyl, tolyl, benzyl, and derivatives thereof, but are not particularly limited thereto.

More specific examples of such silver compounds include the following structures 1 to 15:

[Structure 1]

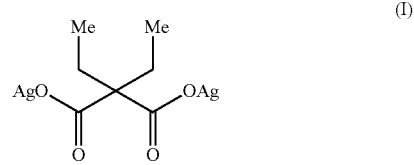
(I)

[Structure 2]

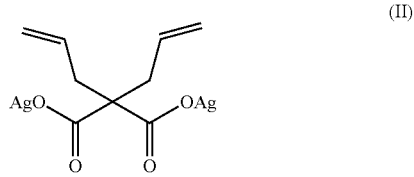
(II)

[Structure 3]

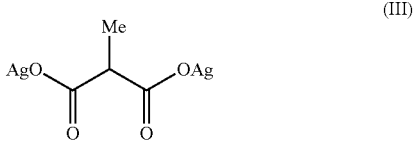
(III)

[Structure 4]

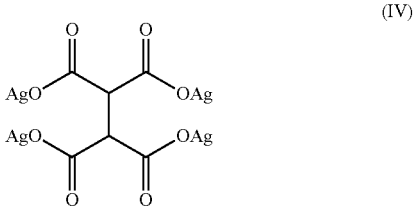
(IV)

[Structure 5]

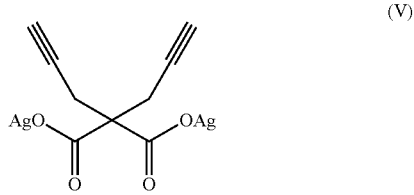
(V)

[Structure 6]

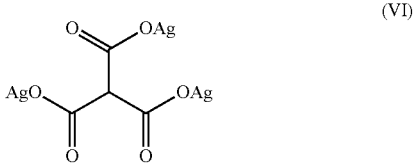
(VI)

[Structure 7]

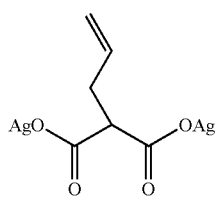
(VII)

[Structure 8]

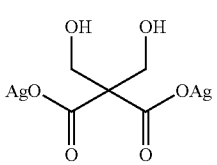
(VIII)

[Structure 9]

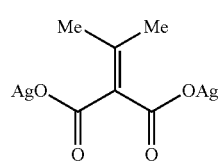
(IX)

[Structure 10]

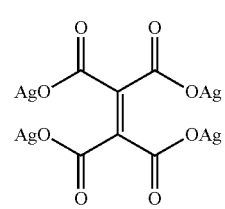
(X)

[Structure 11]

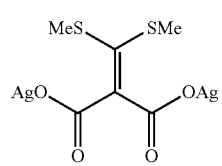
(XI)

[Structure 12]

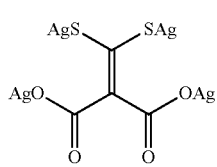
(XII)

[Structure 13]

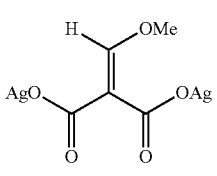
(XIII)

[Structure 14]

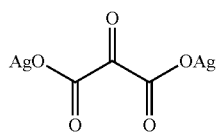
(XIV)

[Structure 15]

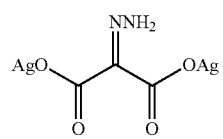
(XV)

There is no particular restriction on the structure and preparation method of the silver precursor compound. For example, the silver precursor may be prepared by the following procedure. First, starting materials for the silver precursor are prepared by methods described in the literature or suitable modifications thereof. The materials may be directly prepared and used when they are not known or their preparation methods are not described in the literature. Representative methods for preparing the silver precursor compound are depicted in the following schemes 1 to 6:

[Scheme 1]

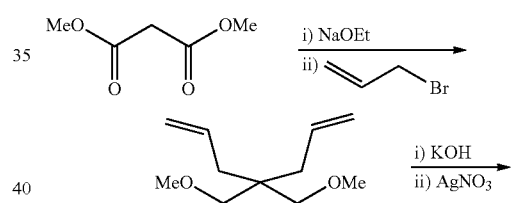

[Scheme 2]

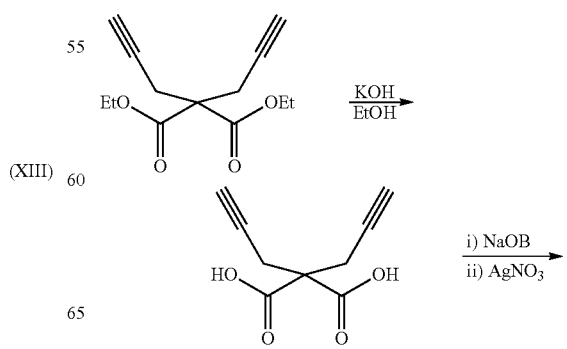

-continued

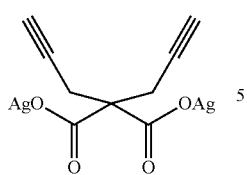

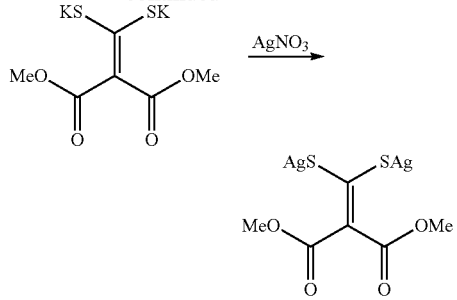

[Scheme 3]

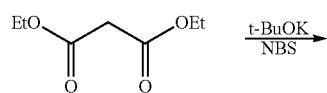

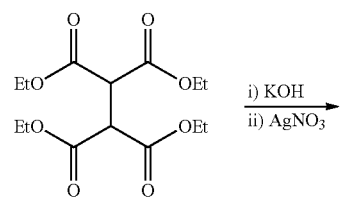

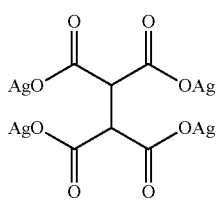

[Scheme 6]

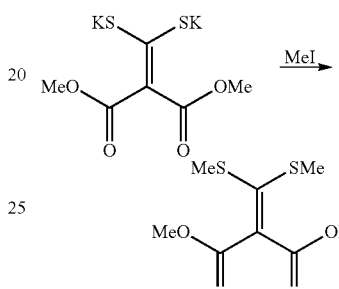

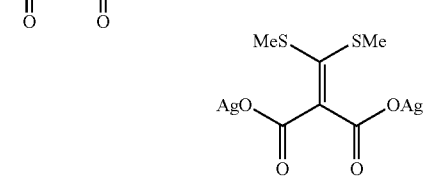

[Scheme 4]

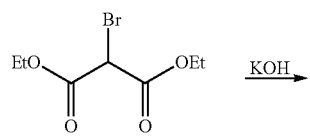

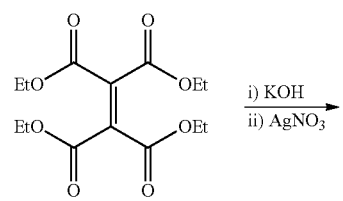

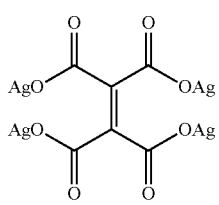

[Scheme 5]

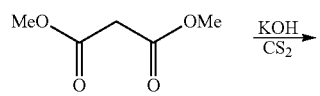

Main starting materials shown in Schemes 1 to 6 may be purchased from those that are already commercially prepared and sold or may be prepared by general methods known in the literature. The silver precursor may be prepared by different methods depending on the kind of the silver or the silver salt. However, any method that does not impair the object of the present invention may be used to prepare the silver precursor. For example, the silver precursor may be prepared by reacting a methyl or ethyl ester with potassium hydroxide in ethanol solution to form a corresponding potassium salt and adding an aqueous solution of silver nitrate thereto. Alternatively, the silver precursor may be prepared by converting a methyl or ethyl ester to a corresponding carboxylic acid, neutralizing the carboxylic acid with an aqueous solution of sodium hydroxide, and adding silver nitrate thereto. Herein, it should be particularly noted that when the reaction mixture has a very high pH, that is, it is strongly basic, it tends to oxidize the silver nitrate. To prevent this oxidation, it is essential to neutralize the reaction mixture using a dilute aqueous solution of nitric acid before reaction with the silver nitrate.

As can be seen from the foregoing structures and schemes, the silver precursor may have various structures and molecular weights so long as the object of the present invention is not impaired. A more preferred structure of the silver precursor is obtained when the silver precursor has a higher silver content, is more highly soluble and stable, and has better ability to form a high quality silver thin film.

Methods for preparing the compounds and precursors shown in the foregoing structures and schemes will be explained in more detail in the Examples section that follows.

Various compounds, such as solvents and additives, are required to produce inks from the silver precursors.

For example, a complexing agent or a ligand is generally required to dissolve more easily dissolve a higher concentration of the silver precursor in a general solvent. Such complexing agents or ligands are mostly electron donors well known in the art, and examples thereof include amine compounds, mercaptan compounds, and phosphine compounds, which are all sigma-electron donors and are known to be involved in complex formation. These compounds may be used in combination as a mixture thereof.

The amine compounds may be, for example, primary amines, secondary amines, tertiary amines, and/or quaternary ammonium salts. The amines may be substituted with alkyl, aryl or aralkyl. Particularly, the alkyl may be linear, branched or cyclic. The amines may also be multi-amines or amines having a functional group, such as a hydroxyl, alkoxy, ester, amide or urethane group. Specific examples of the amines include ammonia, methylamine, ethylamine, n-propylamine, isopropylamine, n-butylamine, isobutylamine, t-butylamine, isoamylamine, n-hexylamine, diethylamine, triethylamine, amylamine, 2-ethylhexylamine, cyclohexylamine, allylamine, propargylamine, ethylenediamine, monoethanolamine, diethanolamine, 1-amino-2-propanol, 3-amino-1-propanol, 2-amino-2-methyl-1-propanol, 2-amino-2-ethyl-1,3-propanediol, N,N-diethylhydroxyamine, methoxyethylamine, N,N-diethylethylenediamine, N,N,N',N'-tetramethylethylenediamine, pyridine, morpholine, imidazole, benzylamine, phenethylamine, ammonium carbamate, ammonium carbonate, tetraethylammonium bicarbonate, tetraethylammonium bromide, tetrabutylammonium hydroxide, polyethyleneimine, polyvinylamine, aminopropyltriethoxysilane, and derivatives thereof. The number of carbon atoms of the amines is preferably 20 or lower but is not particularly limited thereto.

Examples of the phosphine compounds include trimethylphosphine, tributylphosphine, and triphenylphosphine. Representative examples of the sulfur compounds include ethanethiol, dodecylthiol, dimethyl sulfide, tetrahydrothiophene, bismuthiol, and mercaptopropyltrimethoxysilane.

Phi-electron donors are also involved in complex formation and are mostly compounds having a double or triple bond. Some phi-electron donors can strongly form complexes and some can weakly form complexes. Accordingly, suitable phi-electron donors can be selected according to the intended needs. Examples of the phi-electron donors include cyclooctadiene, butadiene, norbornadiene, allyl alcohol, vinyltriethylsilane, propargyl alcohol, 1-ethynylcyclohexanol, 3-butyn-2-ol, 2-methyl-3-butyn-2-ol, 3-methyl-1-pentyn-3-ol, and 3,5-dimethyl-1-hexyn-3-ol (Surfynol 61).

The amount of each electron donor used is not necessarily limited but is typically in the range of 0.5 to 95% by weight, preferably 0.5 to 50% by weight, more preferably 0.5 to 25% by weight, based on the weight of the silver precursor.

The silver ink of the present invention may further include one or more additives selected from the group consisting of solvents, resins, stabilizers, dispersants, reducing agents, coupling agents, leveling agents, surfactants, wetting agents, thickeners, and thixotropic agents, which are required to control the viscosity of the ink or facilitate the formation of a thin film.

Specific examples of the solvents include water, methanol, ethanol, isopropanol, butanol, benzyl alcohol, diacetone alcohol, methoxyethanol, ethoxyethanol, butoxyethanol, ethylene glycol, diethylene glycol, propylene glycol monomethyl ether, monoglyme, diglyme, butyl carbitol, α-terpineol, glycerin, ethyl acetate, butyl acetate, ethyl lactate, carbitol acetate, acetone, methyl ethyl ketone, cyclohexanone, chloroform, methylene chloride, diethyl ether, tetrahydrofuran, dioxane, hexane, cyclohexane, heptane, dimethylformamide, dimethylacetamide, dimethyl sulfoxide, N-methylpyrrolidone, benzene, toluene, and xylene. These solvents may be used alone or as a mixture thereof. Examples of the resins include acrylic resins, polyvinyl resins, polyolefin resins, polyester resins, polyamide resins, polyurethane resins, polysulfone resins, epoxy resins, phenolic resins, phenoxy resins, alkyd resins, melamine resins, urea resins, silicone resins, fluorinated resins, and cellulose resins. Other examples of the resins include water-soluble resins, thermoplastic resins, thermosetting resins, and UV curable resins. The resins may be, for example, latex and natural resins. The stabilizers serve to stabilize the ink. Examples of the stabilizers include organic acids, such as formic acid, acetic acid, propionic acid, and para-toluenesulfonic acid, inorganic acids, such as sulfuric acid and phosphoric acid, fatty acids, such as neodecanoic acid and stearic acid, and acid derivatives, such as fatty acid metal salts. The reducing agents may be, for example, hydrazine, sodium borohydride, hydroquinone, formic acid, formaldehyde, ammonium formate, triethylammonium formate, tetramethylammonium formate, glucose, citric acid, and ascorbic acid. The surfactants are typically nonionic, anionic, cationic, and amphoteric surfactants. As the wetting agents, there may be used, for example, ethylene glycol, propylene glycol, butanediol, pentanediol, hexanediol, polyethylene glycol, and Surfynol series available from Air Products. As the thickeners, there may be used, for example, hydroxypropyl cellulose and Bentone. As the leveling agents, there may be used, for example, BYK series. However, the amounts of these additives used are not particularly limited so long as the characteristics of the ink according to the present invention are not sacrificed.

The silver ink of the present invention is not necessarily limited to a particular viscosity so long as a thin film and a pattern can be formed by suitable coating and printing techniques without causing any problem. The viscosity of the silver ink is preferably from 0.1 to 1,000,000 cps, more preferably from 1 to 100,000 cps. Particularly, in the case of gravure or roll-to-roll printing, the viscosity of the ink may be in the range of 0.1 to 2,000 cps, as measured at room temperature (20° C.). Also in the case where a thin film and a pattern are formed by inkjet printing, the viscosity of the ink is very important. In this case, the viscosity of the ink is typically in the range of 0.1 to 50 cps, preferably 1 to 20 cps, more preferably 3 to 15 cps, as measured at room temperature (20° C.). If the viscosity of the ink is less than the lower limit defined above, the ink may spread or the thickness of a thin film after calcination is not sufficient, tending to deteriorate the conductivity of the thin film. Meanwhile, if the viscosity of the ink exceeds the upper limit defined above, the ink is not readily ejected through a nozzle.

So long as the object of the present invention is not impaired, the method for producing the silver ink of the present invention is not particularly limited. For example, there is no particular restriction on the solvent, reaction temperature, concentration, pressure or whether a catalyst is used.

The silver ink of the present invention can be used to produce hybrid inks. Specifically, hybrid inks may be produced by mixing or reacting the ink of the present invention with one or more materials selected from the group consisting of other known metal precursor compounds, metal powders, metal nanoparticles, metal wires, carbon nanotubes, graphene, conductive polymers, and inks produced therefrom.

Examples of such materials include silver formate, silver acetate, silver trifluoroacetate, silver 1,3-acetonedicarboxylate, silver acetoacetate, silver oxalate, silver lactate, silver malonate, silver malate, silver maleate, silver fumarate, silver glyoxylate, silver pyruvate, silver succinate, silver glutalate, silver gluconate, silver picrate, silver citrate, silver iminodiacetate, silver nitrilotriacetate, silver ethylenediaminetetraacetate, silver neodecanoate, silver stearate, silver oxide, silver carbonate, micro- and nanoparticles of silver, copper, or nickel, and nano- and paste inks of silver or copper.

The silver ink may be deposited by a suitable coating or printing technique to form a thin film. The coating or printing technique can be selected from spin coating, pipetting, blade coating, bar coating, rod coating, roll coating, spray coating, curtain coating, dip coating, flow coating, comma coating, slot die coating, dispensing, casting, stamping, imprinting, pad printing, inkjet printing, offset printing, screen printing, gravure printing, flexography printing, and lithography.

The coated thin film or patterned film may be chemically treated with a liquid or vapor phase acidic or basic compound or a chemical, such as an oxidizing agent or a reducing agent. Alternatively, the coated thin film or patterned film may be physically treated. For example, the coated thin film or patterned film may be treated with heat, plasma, IR, UV, electron beam, laser or microwave or may be electrically or magnetically treated. A combination of the chemical and physical treatments may be applied to the coated thin film or patterned film. This post-treatment makes the film highly conductive in a more rapid manner.

The post-treatment process may be carried out under heating in a general inert atmosphere. If needed, the post-treatment process may be carried out in air, nitrogen, carbon monoxide, a hydrogen/air mixture or a mixed gas thereof. The post-treatment is typically performed at 400° C. or less, preferably 250° C. or less. The post-treatment temperature may be increased or decreased depending on the kind of a substrate used. The post-treatment time is not particularly limited but is preferably as short as possible so long as serious problems are not caused in a batch or continuous process.

The present invention will be explained with reference to the following examples. However, these examples are merely illustrative and the scope of the present invention is not limited thereto.

EXAMPLES

Preparation of Silver Precursors

Example 1

Preparation of Silver Diethylmalonate 6.89 g (0.043 mol) of diethylmalonic acid was dissolved in 100 ml of methanol and an aqueous solution of 3.60 g (0.09 mol) of sodium hydroxide (NaOH) in 100 ml of water was slowly added thereto with stirring. The mixture was allowed to react with stirring at room temperature for 3 h. The reaction mixture was adjusted to pH 7.0 with a dilute aqueous solution of nitric acid and then a solution of 15.29 g (0.09 mol) of silver nitrate ($AgNO_3$) in 100 ml of water was slowly added dropwise thereto to precipitate a white solid. The precipitate was filtered, sufficiently washed sequentially with water and methanol, and dried in a vacuum oven, affording 15.93 g (yield 99.1%) of the title product as a white solid.

Example 2

Preparation of Silver Diallylmalonate 25.48 g (0.12 mol) of dimethyl diallylmalonate was added to 250 ml of a 10% ethanolic KOH solution. The mixture was allowed to react under reflux for 12 h. After completion of the reaction, the reaction mixture in the form of a slurry was dissolved in 250 ml of distilled water to obtain a transparent solution. A dilute aqueous solution of nitric acid was added to the transparent solution until the pH reached 7.0 and then an aqueous solution of 42.47 g (0.25 mol) of silver nitrate ($AgNO_3$) in 150 mL of water was slowly added dropwise to precipitate a white solid. The precipitate was filtered, sufficiently washed sequentially with water and methanol, and dried in a vacuum oven, affording 45.85 g (yield 96%) of the title product as a white solid.

Example 3

Preparation of Silver Methylmalonate 5.08 g (0.043 mol) of methylmalonic acid was dissolved in 100 ml of methanol and a solution of 3.60 g (0.09 mol) of sodium hydroxide (NaOH) in 100 ml of water was slowly added thereto with stirring. The mixture was allowed to react with stirring at room temperature for 3 h. The reaction mixture was adjusted to pH 7.0 with a dilute aqueous solution of nitric acid and then a solution of 15.29 g (0.09 mol) of silver nitrate ($AgNO_3$) in 100 ml of water was slowly added dropwise thereto to precipitate a white solid. The precipitate was filtered, sufficiently washed sequentially with water and methanol, and dried in a vacuum oven, affording 13.80 g (yield 96.7%) of the title product as a white solid.

Example 4

Preparation of Silver Allylmalonate 24.02 g (0.12 mol) of diethyl allylmalonate was added to 500 ml of a 5% ethanolic KOH solution. The mixture was allowed to react under reflux for 12 h. After completion of the reaction, the reaction mixture in the form of a slurry was dissolved in 250 ml of distilled water to obtain a transparent solution. A dilute aqueous solution of nitric acid was added to the transparent solution until the pH reached 7.0 and then an aqueous solution of 42.47 g (0.25 mol) of silver nitrate ($AgNO_3$) in 150 mL of water was slowly added dropwise to precipitate a white solid. The precipitate was filtered, sufficiently washed sequentially with water and methanol, and dried in a vacuum oven, affording 42.30 g (yield 98.5%) of the title product as a white solid.

Example 5

Preparation of Silver Ethanetetracarboxylate 19.10 g (0.06 mol) of ethyl ethanetetracarboxylate was added to 250 ml of a 10% ethanolic KOH solution. The mixture was allowed to react under reflux for 12 h. After completion of the reaction, the reaction mixture in the form of a slurry was dissolved in 200 ml of distilled water to obtain a transparent solution. A dilute aqueous solution of nitric acid was added to the transparent solution until the pH reached 7.0 and then an aqueous solution of 42.47 g (0.25 mol) of silver nitrate in 150 mL of water was slowly added dropwise to precipitate a white solid. The precipitate was filtered, sufficiently washed sequentially with water and methanol, and dried in a vacuum oven, affording 34.72 g (yield 91.3%) of the title product as a white solid.

Example 6

Preparation of Silver Dipropargylmalonate 10.20 g (0.058 mol) of dipropargylmalonic acid was dissolved in 100 ml of methanol and a solution of 4.80 g (0.12 mol) of sodium hydroxide (NaOH) in 100 ml of water was slowly added thereto with stirring. The mixture was allowed to react with stirring at room temperature for 3 h. The reaction mixture was adjusted to pH 7.0 with a dilute aqueous solution of nitric acid and then a solution of 20.38 g (0.12 mol) of silver nitrate ($AgNO_3$) in 100 ml of water was slowly added dropwise thereto to precipitate a white solid. The precipitate was filtered, sufficiently washed sequentially with water and methanol, and dried in a vacuum oven, affording 22.40 g (yield 97.5%) of the title product as a white solid.

Example 7

Preparation of Silver Methanetricarboxylate 27.87 g (0.12 mol) of triethyl methanetricarboxylate was added to 400 ml of a 10% ethanolic KOH solution. The mixture was allowed to react under reflux for 12 h. After completion of the reaction, the reaction mixture in the form of a slurry was dissolved in 300 ml of distilled water to obtain a transparent solution. A dilute aqueous solution of nitric acid was added to the transparent solution until the pH reached 7.0 and then an aqueous solution of 67.95 g (0.40 mol) of silver nitrate in 200 ml of water was slowly added dropwise to precipitate a white solid. The precipitate was filtered, sufficiently washed sequentially with water and methanol, and dried in a vacuum oven, affording 53.45 g (yield 95.0%) of the title product as a white solid.

Example 8

Preparation of Silver Isopropylidenemalonate 24.03 g (0.12 mol) of diethyl isopropylidenemalonate was added to 250 ml of a 10% ethanolic KOH solution. The mixture was allowed to react under reflux for 12 h. After completion of the reaction, the reaction mixture in the form of a slurry was dissolved in 250 ml of distilled water to obtain a transparent solution. A dilute aqueous solution of nitric acid was added to the transparent solution until the pH reached 7.0 and then an aqueous solution of 42.47 g (0.25 mol) of silver nitrate ($AgNO_3$) in 150 ml of water was slowly added dropwise to precipitate a white solid. The precipitate was filtered, sufficiently washed sequentially with water and methanol, and dried in a vacuum oven, affording 44.31 g (yield 89.2%) of the title product as a white solid.

Example 9

Preparation of Silver Bis(Hydroxymethyl)Malonate 26.43 g (0.12 mol) of diethyl bis(hydroxymethyl)malonate was added to 250 ml of a 10% ethanolic KOH solution. The mixture was allowed to react under reflux for 12 h. After completion of the reaction, the reaction mixture in the form of a slurry was dissolved in 250 ml of distilled water to obtain a transparent solution. A dilute aqueous solution of nitric acid was added to the transparent solution until the pH reached 7.0 and then an aqueous solution of 42.47 g (0.25 mol) of silver nitrate ($AgNO_3$) in 150 ml of water was slowly added dropwise to precipitate a white solid. The precipitate was filtered, sufficiently washed sequentially with water and methanol, and dried in a vacuum oven, affording 39.69 g (yield 87.5%) of the title product as a white solid.

Example 10

Preparation of Silver Ethylenetetracarboxylate 9.49 g (0.03 mol) of ethyl ethylenetetracarboxylate was added to 125 ml of a 10% ethanolic KOH solution. The mixture was allowed to react under reflux for 12 h. After completion of the reaction, the reaction mixture in the form of a slurry was dissolved in 100 ml of distilled water to obtain a transparent solution. A dilute aqueous solution of nitric acid was added to the transparent solution until the pH reached 7.0 and then an aqueous solution of 22.06 g (0.13 mol) of silver nitrate in 100 ml of water was slowly added dropwise to precipitate a white solid. The precipitate was filtered, sufficiently washed sequentially with water and methanol, and dried in a vacuum oven, affording 17.53 g (yield 92.5%) of the title product as a white solid.

Example 11

Preparation of Silver [Bis(Methylthio)Methylene]Malonate 5.36 g (0.02 mol) of methyl [bis(methylthio)methylene] malonate as a white solid, which had been purified by recrystallization from ethanol, was added to 100 ml of a 5% ethanolic KOH solution. The mixture was allowed to react under reflux for 12 h. After completion of the reaction, the reaction mixture in the form of a slurry was dissolved in 100 ml of distilled water to obtain a transparent solution. A dilute aqueous solution of nitric acid was added to the transparent solution until the pH reached 7.0 and then an aqueous solution of 6.80 g (0.04 mol) of silver nitrate in 100 ml of distilled water was slowly added dropwise to precipitate a solid. The precipitate was filtered, sufficiently washed sequentially with water and methanol, and dried in a vacuum oven, affording 8.48 g (yield 93.5%) of the title product as a solid.

Example 12

Preparation of Methyl [Bis(Silver Thio)Methylene]Malonate 3.60 g (0.02 mol) of methyl [bis(potassium thio)methylene]malonate as a yellow solid was dissolved in 50 ml of distilled water and an aqueous solution of 6.80 g (0.04 mol) of silver nitrate in 50 ml of water was slowly added thereto to precipitate a solid. The precipitate was filtered, sufficiently washed sequentially with water and methanol, and dried in a vacuum oven, affording 8.69 g (yield 95.8%) of the title product as a solid.

Example 13

Preparation of Silver Mesoxalate 6.32 g (0.02 mol) of sodium mesoxalate monohydrate was dissolved in 50 ml of distilled water and then an aqueous solution of 6.80 g (0.04 mol) of silver nitrate in 50 ml of water was slowly added dropwise thereto to precipitate a white solid. The precipitate was filtered, sufficiently washed sequentially with water and methanol, and dried in a vacuum oven, affording 6.25 g (yield 94.3%) of the title product as a solid.

Example 14

Preparation of Silver Mesoxalate Hydrazone 22.56 g (0.12 mol) of diethyl mesoxalate was added to 250 ml of a 10% ethanolic KOH solution. The mixture was allowed to react under reflux for 12 h. After completion of the reaction, the reaction mixture in the form of a slurry was dissolved in 250 ml of distilled water to obtain a transparent solution. A dilute aqueous solution of nitric acid was added to the transparent solution until the pH reached 7.0 and then an aqueous solution of 42.47 g (0.25 mol) of silver nitrate ($AgNO_3$) in 150 ml of water was slowly added dropwise to precipitate a solid. The precipitate was filtered, sufficiently washed sequentially with water and methanol, and dried in a vacuum oven, affording 38.17 g (yield 92.0%) of the title product as a solid.

Production and Evaluation of Silver Inks

Example 15

4.0 g of isobutylamine was mixed with 2.0 g of the silver precursor compound (i.e. silver diethylmalonate) prepared in Example 1 and then 0.4 g of aqueous ammonia (ammonia content 28-30 wt %) was slowly added dropwise thereto with sufficient stilling. To the resulting mixture were sequentially added 0.8 g of 50% aqueous ammonium formate, 1.0 g of methanol, and 0.4 g of 2-amino-2-methyl-1-propanol. After sufficient mixing, the solution was passed through a 0.45 micron Teflon filter to obtain a transparent silver ink. The silver ink was found to have a viscosity of 7.8 cps and a surface tension of 27.1 dyne/cm. The composition was stable at room temperature and in air. The composition was spin coated on a glass substrate using a spin coater and sintered at 230° C. for 20 min to form a silver film. The film was measured to have a conductivity of $0.3\Omega/\Box$.

Example 16

4.0 g of isobutylamine was mixed with 2.0 g of the silver precursor compound (i.e. silver diallylmalonate) prepared in Example 2 and then 0.4 g of aqueous ammonia (ammonia content 28-30 wt %) was slowly added dropwise thereto with sufficient stilling. To the resulting mixture were sequentially added 0.8 g of 50% aqueous ammonium formate, 1.0 g of methanol, and 0.4 g of 2-amino-2-methyl-1-propanol. After sufficient mixing, the solution was passed through a 0.45 micron Teflon filter to obtain a transparent silver ink. The silver ink composition was spin coated on a PET film using a spin coater and sintered at 140° C. for 10 min to form a mirror-like silver film. The film was measured to have a conductivity of $1.2\Omega/\Box$.

Example 17

2.0 g of aqueous ammonia (ammonia content 28-30 wt %) was slowly added dropwise to 2.0 g of the silver precursor compound (i.e. silver methylmalonate) prepared in Example 3 with sufficient stirring. To the mixture were sequentially added 0.8 g of 50% aqueous ammonium formate, 0.4 g of 2,3-butanediol, and 0.4 g of 2-amino-2-methyl-1-propanol. After sufficient mixing, the solution was passed through a 0.45 micron Teflon filter to obtain a transparent silver ink. The silver ink composition was spin coated on a PET film using a spin coater and sintered at 140° C. for 10 min to form a silver film. The film was measured to have a conductivity of $1.7\Omega/\Box$.

Example 18

4.0 g of isobutylamine was mixed with 2.0 g of the silver precursor compound (i.e. silver allylmalonate) prepared in Example 4 and then 0.4 g of aqueous ammonia (ammonia content 28-30 wt %) was slowly added dropwise thereto with sufficient stilling. To the resulting mixture were sequentially added 0.8 g of 50% aqueous ammonium formate, 1.0 g of methanol, and 0.4 g of 2-amino-2-methyl-1-propanol. After sufficient mixing, the solution was passed through a 0.45 micron Teflon filter to obtain a transparent silver ink. The silver ink was found to have a viscosity of 7.5 cps and a surface tension of 27.0 dyne/cm. The composition was stable at room temperature and in air. The composition was spin coated on a glass substrate using a spin coater and sintered at 230° C. for 15 min to form a silver film. The film was measured to have a conductivity of $0.2\Omega/\Box$.

Example 19

5.0 g of aqueous ammonia (ammonia content 28-30 wt %) was slowly added dropwise to 3.0 g of the silver precursor compound (i.e. silver ethanetetracarboxylate) prepared in Example 5 with sufficient stirring. To the mixture were sequentially added 0.8 g of triethylammonium formate, 0.5 g of 2-amino-2-ethyl-1-propanediol, and 2.0 g of methanol. After sufficient mixing, the solution was passed through a 0.45 micron Teflon filter to obtain a transparent silver ink. The silver ink composition was spin coated on a glass substrate using a spin coater and sintered at 230° C. for 15 min to form a silver film. The film was measured to have a conductivity of $0.5\Omega/\Box$.

Example 20

4.0 g of isobutylamine was mixed with 2.0 g of the silver precursor compound (i.e. silver dipropargylmalonate) prepared in Example 6 and then 0.4 g of aqueous ammonia (ammonia content 28-30 wt %) was slowly added dropwise thereto with sufficient stirring. To the resulting mixture were sequentially added 0.5 g of 50% aqueous ammonium formate, 1.0 g of methanol, and 0.4 g of 2-amino-2-methyl-1-propanol. After sufficient mixing, the solution was passed through a 0.45 micron Teflon filter to obtain a transparent silver ink. The silver ink composition was spin coated on a PET film using a spin coater and sintered at 150° C. for 10 min to form a silver film. The film was measured to have a conductivity of 1.5Ω/□.

Example 21

3.0 g of isobutylamine was mixed with 2.0 g of the silver precursor compound (i.e. silver isopropylidenemalonate) prepared in Example 8 and then 0.5 g of aqueous ammonia (ammonia content 28-30 wt %) was slowly added dropwise thereto with sufficient stirring. To the resulting mixture were sequentially added 0.5 g of 50% triethylammonium formate, 0.5 g of 2-amino-2-ethyl-1-propanediol, and 0.5 g of methanol. After sufficient mixing, the solution was passed through a 0.45 micron Teflon filter to obtain a transparent silver ink. The silver ink composition was spin coated on a PET film using a spin coater and sintered at 150° C. for 20 min to form a silver film. The film was measured to have a conductivity of 1.1 Ω/□.

Example 22

5.0 g of aqueous ammonia (ammonia content 28-30 wt %) was slowly added dropwise to 3.0 g of the silver precursor compound (i.e. silver ethylenetetracarboxylate) prepared in Example 10 with sufficient stirring. To the mixture were sequentially added 0.8 g of ammonium formate, 0.5 g of 2,3-butanediol, 0.5 g of 2-amino-2-methyl-1-propanol, and 1.0 g of methanol. After sufficient mixing, the solution was passed through a 0.45 micron Teflon filter to obtain a transparent silver ink. The silver ink composition was spin coated on a glass substrate using a spin coater and sintered at 230° C. for 15 min to form a silver film. The film was measured to have a conductivity of 0.8 Ω/□.

Example 23

5.0 g of aqueous ammonia (ammonia content 28-30 wt %) was slowly added dropwise to 3.0 g of the silver precursor compound (i.e. silver mesoxalate) prepared in Example 13 with sufficient stirring. To the mixture were sequentially added 0.8 g of ammonium formate, 0.5 g of 2-amino-2-ethyl-1-propanediol, and 1.0 g of methanol. After sufficient mixing, the solution was passed through a 0.45 micron Teflon filter to obtain a transparent silver ink. The silver ink composition was spin coated on a glass substrate using a spin coater and sintered at 230° C. for 15 min to form a silver film. The film was measured to have a conductivity of 0.4 Ω/□.

Example 24

3.0 g of isobutylamine and 0.5 g of aqueous ammonia (ammonia content 28-30 wt %) were slowly added dropwise to a mixture of 1.0 g of the silver precursor compound (i.e. silver diethylmalonate) prepared in Example 1 and 1.0 g of the silver precursor compound (i.e. silver diallylmalonate) prepared in Example 2 with sufficient stilling. To the mixture were sequentially added 0.8 g of 50% aqueous ammonium formate, 0.5 g of 2-amino-2-ethyl-1-propanediol, and 1.0 g of methanol. After sufficient mixing, the solution was passed through a 0.45 micron Teflon filter to obtain a transparent silver ink. The silver ink composition was spin coated on a PET film and sintered at 150° C. for 20 min to form a silver film. The film was measured to have a conductivity of 1.5Ω/□.

Example 25

2.0 g of aqueous ammonia (ammonia content 28-30 wt %) was slowly added dropwise to a mixture of 1.0 g of the silver precursor compound (i.e. silver methylmalonate) prepared in Example 3 and 1.0 g of silver acetate with sufficient stilling. To the resulting mixture were sequentially added 0.8 g of 50% aqueous ammonium formate, 0.4 g of 2-amino-2-methyl-1-propanediol, and 0.4 g of 2-amino-2-methyl-1-propanol. After sufficient mixing, the solution was passed through a 0.45 micron Teflon filter to obtain a transparent silver ink. The silver ink was found to have a viscosity of 7.5 cps and a surface tension of 27.6 dyne/cm. The composition was stable at room temperature and in air and was inkjet printable. The composition was spin coated on a PET film using a spin coater and sintered at 150° C. for 10 min to form a silver film. The film was measured to have a conductivity of 1.1Ω/□.

<Measurements and Evaluations>

1) Conductivity was evaluated by measuring the sheet resistance of a patterned rectangular sample (1 cm×3 cm) of each film using a four-point probe (CMT-SR1000N, AIT).

2) Stability was evaluated by observing whether silver was reduced after standing of each ink at room temperature for at least 48 h.

3) Inkjet printability was evaluated by ejecting each ink at room temperature with a Dimatix DMP-2831 (10 pl nozzle) inkjet printer.

4) Viscosity was measured using a Brookfield DV-II+ PRO LV (spindle: CPE-40) viscometer.

5) Surface tension was measured using a tension meter (Surface Tensiomat 21)

The invention claimed is:
1. A silver ink comprising a silver malonate precursor represented by Formula 1:

[Formula 1]

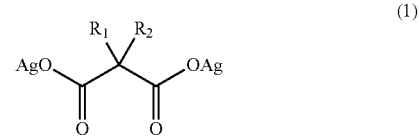

(1)

wherein $R_1$ and $R_2$, except that both $R_1$ and $R_2$ are hydrogen, are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, substituted or unsubstituted $C_5$-$C_{30}$ heteroaralkyl, —$(CH_2)_j OR^a$, —$(CH_2)_j C(O)R^a$, —$(CH_2)_j C(O)OR^a$, —$(CH_2)_j OC(O)R^a$, —$CH(C(O)OAg)_2$, —$(CH_2)_j OAg$, —$(CH_2)_j C(O)Ag$, —$(CH_2)_j C(O)OAg$, —$(CH_2)_j OC(O)Ag$, —$(CH_2)_j NR^b R^c$, —$(CH_2)_j C(O)NR^b R^c$, —$(CH_2)_j OC(O)NR^b R^c$, —$(CH_2)_j NR^d C(O)R^b$, —$(CH_2)_j NR^d C(O)OR^b$, —$(CH_2)_j R^d C(O)NR^b R^c$, —$(CH_2)_j S(O)_m R^e$ or —$(CH_2)_j NR^d S(O)_m Ag$ where j is an integer from 0 to 12, m is an integer from 0 to 2, and $R^a$, $R^b$, $R^c$, $R^d$, and $R^e$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, or substituted or unsubstituted $C_5$-$C_{30}$ heteroaralkyl.

2. The silver ink according to claim 1, wherein the silver malonate precursor is selected from the following structures 1 to 8:

[Structure 1]

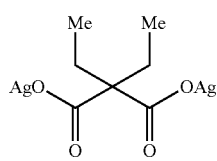

(I)

[Structure 2]

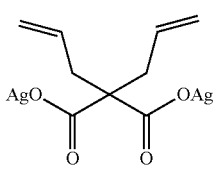

(II)

[Structure 3]

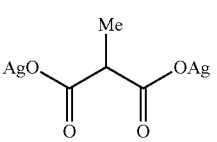

(III)

[Structure 4]

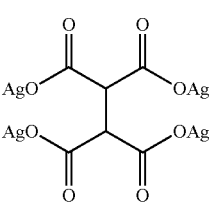

(IV)

[Structure 5]

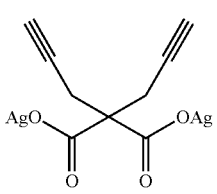

(V)

[Structure 6]

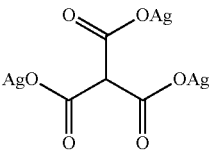

(VI)

-continued

[Structure 7]

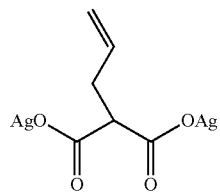

(VII)

[Structure 8]

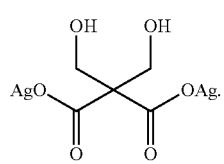

(VIII)

3. The silver ink according to claim 1, wherein $R_1$ and $R_2$, except that both $R_1$ and $R_2$ are hydrogen, are each independently selected from the group consisting of hydrogen, methyl, ethyl, n-propyl, iso-propyl, n-butyl, iso-butyl, t-butyl, n-pentyl, amyl, n-hexyl, 2-ethylhexyl, n-heptyl, octyl, iso-octyl, nonyl, decyl, dodecyl, hexadecyl, octadecyl, docodecyl, cyclopropyl, cyclopentyl, cyclohexyl, allyl, propargyl, acetyl, benzoyl, hydroxyethyl, methoxyethyl, 2-hydroxypropyl, methoxypropyl, aminoethyl, cyanoethyl, mercaptoethyl, chloroethyl, methoxy, ethoxy, butoxy, hexyloxy, phenoxy, methoxyethoxyethyl, methoxyethoxyethoxyethyl, imidazol, carboxymethyl, trimethoxysilylpropyl, triethoxysilylpropyl, phenyl, methoxyphenyl, cyanophenyl, tolyl, benzyl, and derivatives thereof.

4. A silver ink comprising the silver malonate precursor according to claim 1 and one or more additives selected from the group consisting of solvents, complexing agents, resins, stabilizers, dispersants, reducing agents, coupling agents, leveling agents, surfactants, wetting agents, thickeners, and thixotropic agents.

5. The silver ink according claim 4, wherein the ink has a viscosity in the range of 0.1 to 2,000 cps, as measured at room temperature 20° C.

6. A silver ink as a hybrid ink produced by mixing or reacting the silver ink according to claim 4 with one or more materials selected from the group consisting of metal precursor compounds, metal powders, metal nanoparticles, metal wires, carbon nanotubes, graphene, conductive polymers, and inks produced therefrom.

7. The silver ink according claim 6, wherein the ink has a viscosity in the range of 1 to 100,000 cps, as measured at room temperature 20° C.

8. A silver ink comprising a silver malonate precursor represented by Formula 2:

[Formula 2]

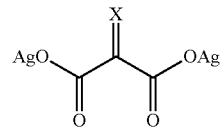

(2)

wherein X is oxygen (O), sulfur (S), $CR_1R_2$, $C(C(O)OAg)_2$, $C(SAg)_2$, $NR_1$ or $NNR_1R_2$; wherein $R_1$ and $R_2$, except that both $R_1$ and $R_2$ are hydrogen, are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, substituted or unsubstituted $C_5$-$C_{30}$ heteroaralkyl, —$(CH_2)_jOR^a$, —$(CH_2)_jC(O)R^3$, —$(CH_2)_jC(O)OR^a$, —$(CH_2)_jOC(O)R^a$, —$CH(C(O)OAg)_2$, —$(CH_2)_jOAg$, —$(CH_2)_jC(O)Ag$, —$(CH_2)_jC(O)OAg$, —$(CH_2)_jOC(O)Ag$, —$(CH_2)_jNR^bR^c$, —$(CH_2)_jC(O)NR^bR^c$, —$(CH_2)_jOC(O)NR^bR^c$, —$(CH_2)_jNR^dC(O)R^b$, —$(CH_2)_jNR^dC(O)OR^b$, —$(CH_2)_jNR^dC(O)NR^bR^c$, —$(CH_2)_jS(O)_mR^e$ or —$(CH_2)_jNR^dS(O)_mA$ where j is an integer from 0 to 12, in is an integer from 0 to 2, and $R^a$, $R^b$, $R^c$, $R^d$, and $R^e$ are each independently hydrogen, halogen, amino, nitro, cyano, hydroxyl, substituted or unsubstituted $C_1$-$C_{30}$ alkyl, substituted or unsubstituted $C_3$-$C_{30}$ cycloalkyl, substituted or unsubstituted $C_6$-$C_{30}$ aryl, substituted or unsubstituted $C_6$-$C_{30}$ aralkyl, substituted or unsubstituted $C_1$-$C_{30}$ heteroalkyl, substituted or unsubstituted $C_2$-$C_{30}$ heterocycloalkyl, substituted or unsubstituted $C_5$-$C_{30}$ heteroaryl, or substituted or unsubstituted $C_5$-$C_{30}$ heteroaralkyl, except that both j and m are zero in case $R_1$ and $R_2$ are each independently —$(CH_2)_jS(O)_mR^e$—.

9. The silver ink according to claim 8, wherein the silver malonate precursor is selected from the following structures 9, 10, and 12-15:

[Structure 9]

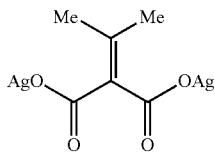

(IX)

[Structure 10]

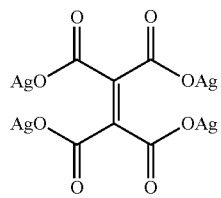

(X)

[Structure 12]

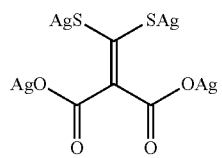

(XII)

[Structure 13]

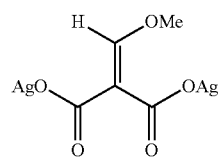

(XIII)

[Structure 14]

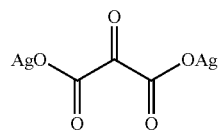

(XIV)

[Structure 15]

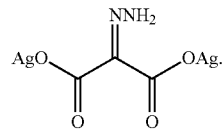

(XV)

10. A silver ink comprising the silver malonate precursor according to claim 8 and one or more additives selected from the group consisting of solvents, complexing agents, resins, stabilizers, dispersants, reducing agents, coupling agents, leveling agents, surfactants, wetting agents, thickeners, and thixotropic agents.

11. The silver ink according to claim 10, wherein the ink has a viscosity in the range of 0.1 to 2,000 cps, as measured at room temperature 20° C.

12. A silver ink as a hybrid ink produced by mixing or reacting the silver ink according to claim 10 with one or more materials selected from the group consisting of metal precursor compounds, metal powders, metal nanoparticles, metal wires, carbon nanotubes, graphene, conductive polymers, and inks produced therefrom.

13. The silver ink according to claim 12, wherein the ink has a viscosity in the range of 1 to 100,000 cps, as measured at room temperature 20° C.

* * * * *